US010973537B2

United States Patent
Mikus et al.

(10) Patent No.: US 10,973,537 B2
(45) Date of Patent: Apr. 13, 2021

(54) METHOD FOR REDUCING BIOFILM FORMATION

(71) Applicant: MISONIX, INC., Farmingdale, NY (US)

(72) Inventors: Paul Mikus, Trabuco Canyon, CA (US); Scott Isola, Deer Park, NY (US); Dan Voic, Cedar Grove, NJ (US); Scott Ludecker, Mount Sinai, NY (US); Alexander Darian, Brightwaters, NY (US)

(73) Assignee: MISONIX, INCORPORATED, Farmingdale, NY (US)

( * ) Notice: Subject to any disclaimer, the term of this patent is extended or adjusted under 35 U.S.C. 154(b) by 408 days.

(21) Appl. No.: 16/126,737

(22) Filed: Sep. 10, 2018

(65) Prior Publication Data

US 2019/0015123 A1    Jan. 17, 2019

Related U.S. Application Data

(62) Division of application No. 14/939,552, filed on Nov. 12, 2015, now Pat. No. 10,092,308.

(60) Provisional application No. 62/078,709, filed on Nov. 12, 2014.

(51) Int. Cl.
*A61B 17/22* (2006.01)
*A61M 1/00* (2006.01)

(52) U.S. Cl.
CPC .. *A61B 17/22004* (2013.01); *A61B 2217/005* (2013.01); *A61M 1/0084* (2013.01); *A61M 2205/058* (2013.01)

(58) Field of Classification Search
CPC .... A61B 17/22004; A61B 2017/00761; A61B 2017/320072; A61B 2017/320084; A61B 2217/005; A61M 1/0084; A61M 2205/058
See application file for complete search history.

(56) References Cited

U.S. PATENT DOCUMENTS

| | | | |
|---|---|---|---|
| 5,139,504 A | 8/1992 | Zelman | A61F 9/00736 606/107 |
| 5,163,433 A | 11/1992 | Kagawa | A61B 17/22012 601/2 |
| 2011/0196403 A1* | 8/2011 | Robertson | A61B 17/22012 606/169 |
| 2013/0046316 A1 | 2/2013 | Sullivan | A61B 10/0275 606/115 |
| 2013/0165821 A1 | 6/2013 | Freedman et al. | |

* cited by examiner

*Primary Examiner* — Kai H Weng
(74) *Attorney, Agent, or Firm* — R. Neil Sudol; Henry D. Coleman

(57) ABSTRACT

A two phase method for reducing the formation of biofilm includes an evacuation of ambient air from a region about the surgical or treatment site, to extract airborne or aerosolized bacteria ejected from the site by the treatment. The extracted bacteria are prevented from settling back onto the cleansed tissue surface, thus at least reducing colonial bacteriological growth and concomitantly exuded biofilm material. A second phase involves the attachment of one or more ultrasonic transducers to the patient over or near a surgical treatment site after the surgery is terminated. Each applied ultrasonic transducer is used to vibrate the patient's tissues at the treatment site to disrupt biofilm formation.

8 Claims, 9 Drawing Sheets

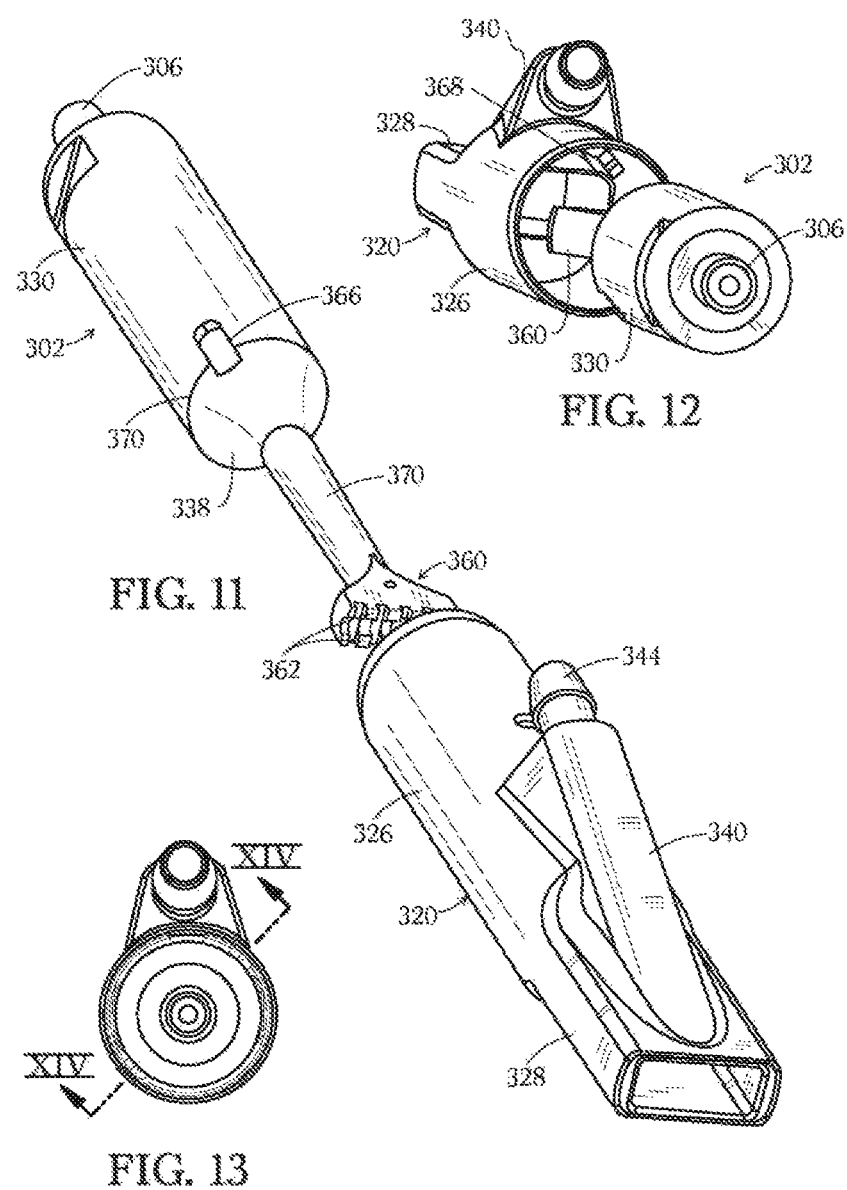

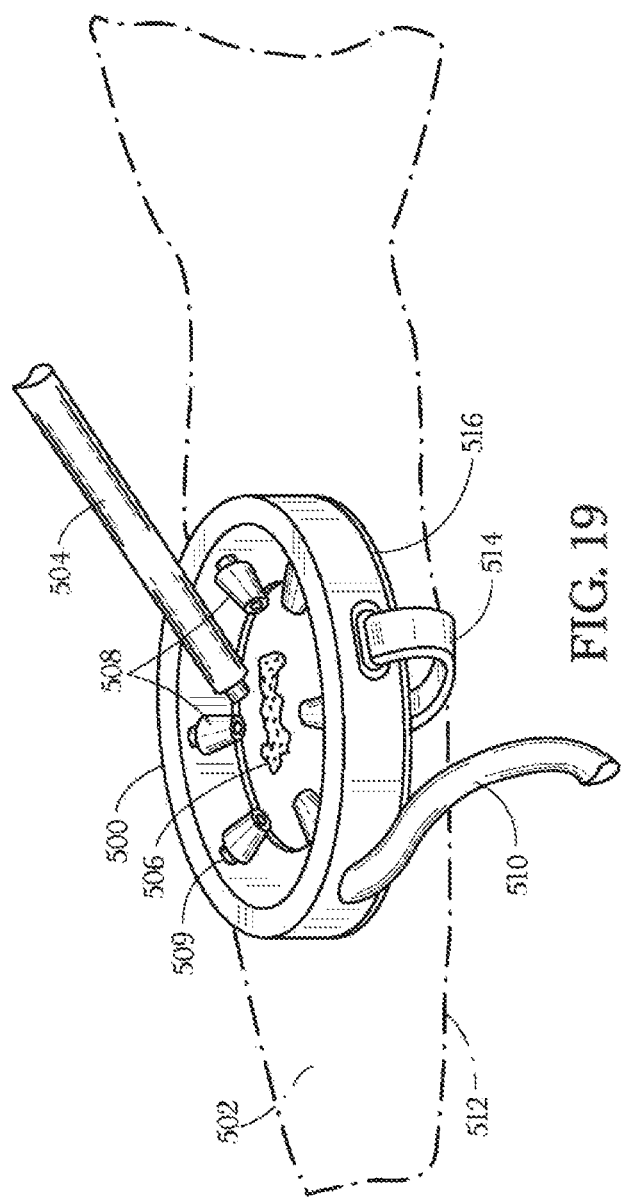

METHOD FOR REDUCING BIOFILM FORMATION

CROSS-REFERENCE TO RELATED APPLICATION

This application is a division of application Ser. No. 14/939,552, now U.S. Pat. No. 10,092,308 filed Nov. 12, 2015. This application also claims the benefit of U.S. Provisional Patent Application No. 62/078,709 filed Nov. 12, 2014.

BACKGROUND OF THE INVENTION

This invention relates to apparatus and method for reducing biofilm on a wound site particularly a wound site that is being debrided to remove necrotic tissue.

Chronic wound infection represents a significant healthcare problem worldwide. Often the end objective of wound healing is the objective for new therapeutic options. Yet chronic wounds compromise a number of different and complex conditions that each interferes with the healing process. For example, a chronic wound can comprise necrotic tissue in need of debridement, bacterial infection in need of antimicrobial agents and compromised vasculature that impedes the normal healing process.

One element of the chronic wound infection condition that impedes healing is the formation of biofilm. Biofilm is the result of planktonic bacteria forming together and secreting exopolysaccharide (EPS) to adhere and protect the colonizing community. At the height of formation, EPS can make up between 75-90% of the total biofilm composition (Regt). Biofilm inhibits healing by creating an optimal condition for bacteria to grow, while simultaneously preventing antimicrobial agents from direct access to bacteria.

Methods to remove biofilm include ultrasonic debridement, topical antimicrobials, suction, and surface cleansing. Each of these methods alone treat an aspect of biofilm. For example, ultrasonic debridement of wounds has proven to be the most effective mechanism in disrupting and debulking a majority of the biofilm formation. Yet even in this preferred method, biofilm debris can be left behind to propagate. Suction alone has not proven to be effective in removing biofilm, and can potentially interfere with the operation of other methods like ultrasonic debridement if applied simultaneously.

U.S. Pat. No. 7,608,054 to Soring et al. describes a medical treatment apparatus that combines an ultrasound sonotrode with a suction sheath. The fixed position between the tip of the suction and the tip of the sonotrode only allows for one simultaneous operation. In particular this approach is limited due to the potential interference of the suction tip during the ultrasonic debridement operation.

U.S. Pat. No. 7,522,955 B2 to Rontal et al. describes a method and apparatus for ultrasonic cleaning of biofilm coated surfaces for sinus cavities within a human head. The method describes an ultrasonic application in combination with irrigation and suction that is designed to not remove any of the surrounding underlying tissue. This differs significantly from an ultrasonic debridement of a wound bed, which requires the removal of tissue in combination with biofilm. Thus the ultrasonic probe needs to operate in a cavitation mode at the surface of a wound, causing destruction of the biofilm.

Methods of mechanical removal of biofilm in wounds alone have proven to be inadequate. What does not exist and what would be beneficial to the market is a method to remove biofilm and prevent it from reforming in order to allow wounds to heal.

OBJECTS OF THE INVENTION

It is an object of the present invention to provide a method to inhibit biofilm formation in order to allow wounds to heal more expeditiously.

A related object of the present invention is to provide a method for removing biofilm so as to reduce the likelihood of the biofilm reforming.

Another related object of the present invention is to provide a method to remove biofilm and prevent it from reforming in order to allow wounds to heal.

An associated object of the present invention is to provide apparatus for removing biofilm with structure to assist in biofilm reformation reduction.

Another associated object of the present invention is to provide apparatus for inhibiting the formation of biofilm.

Although every feature of the invention is attained in at least one embodiment of the invention, there is not necessarily any one embodiment that achieves all of the objects of the invention.

SUMMARY OF THE INVENTION

The present invention broadly contemplates a method for the inhibition of biofilm, a method for reducing the likelihood of biofilm formation. The method includes a surgical room cleansing process and a disruption and removal. The method typically includes a mechanical debridement for the removal of any existing necrotic tissue, surface infection or previously formed biofilm. The mechanical debridement process results in a clean wound bed of healthy granulated tissue. Substantially immediately following the mechanical debridement of a wound, an ultrasound biofilm disrupter pad is placed on or near the wound to prevent bacterial adherence to the wound bed by excretion of EPS.

The ultrasound biofilm disrupter prevents adherence of bacteria to the wound by application of surface acoustic waves at a sufficient frequency and amplitude to disrupt formation but below a threshold that stimulates bacterial growth. In order to accomplish this, a wound-dressing device, which incorporates a disposable ultrasonic transducer, is applied to the wound site post debridement for duration sufficient to allow healing to occur.

In a preferred embodiment ultrasound is used in the debridement process to mechanically remove necrotic tissue while cleansing the wound bed. The ultrasonic debridement should be in the 20 kHz frequency range in order to simultaneously begin the process of biofilm disruption. Once the mechanical debridement is complete, a lower energy setting on the debridement probe may be utilized to pre-condition the wound bed for disrupting adherence or starting the formation of biofilm. Preferably, the wound bed is immediately covered with a wound dressing that incorporates an ultrasonic biofilm disrupter transducer delivering a surface acoustic wave at 20 kHz with an acoustic power output of 0.2-0.4 w/cm$^2$. The transducer is connected to a portable energy source. The energy source can be battery supplied. The wound dressing can incorporate an antimicrobial agent that is delivered during the biofilm disruption treatment.

In another embodiment ultrasound is incorporated into the wound dressing and applied after standard wound cleansing protocols have been administered. These protocols can include saline wash, topical antimicrobial agents applied. The combination of ultrasonic debridement, low-pulsed ultrasonic biofilm disruption and topical antimicrobials produces an important sequential approach to the management and removal of biofilm. The removal of biofilm results in the removal of an impediment to the wound healing process.

In another embodiment ultrasound is combined with suction to create an optimal combination for disruption and removal of biofilm. One stage of biofilm is an excretion of seeding stage. So existing debridement processes can result in a bulking of the biofilm, but at the same time a seeding of the newly created wound bed. The seeding process can occur from a mechanical debridement alone. In this the process for biofilm disruption is temporary at best. To correct this problem, ultrasonic debridement is combined with a suction process that collects the mechanically removed biofilm remnants or seeding agents.

In one embodiment of this combined ultrasound and suction approach, the ultrasonic debridement probe is housed by a suction probe that operates in two stages. The first stage is with the ultrasonic debridement probe engaged with the tissue and the suction tip surrounding the debridement tip so that it is in near contact to the tissue simultaneously to remove the mechanically disrupted biofilm. In the second stage of operation the suction tip can be moved to a position that is not in contact or near contact with the tissue, but sufficient enough to capture any biofilm debris that is propelled into the area.

In another embodiment the combination of ultrasound and suction may have one or more stages of operation. The positioning of the suction tip in relationship to the ultrasound tip can be configured for a variety of different combinations to cause better mechanical disruption and capture of that disrupted biofilm. The combination of both ultrasonic energy to cause debridement and suction to cause removal can be done in a variety of different sequences. For example, ultrasonic mechanical debridement can be performed on the majority of the wound bed prior to engaging suction to capture any remnant amounts of biofilm on the wound bed. In another embodiment the ultrasonic mechanical debridement is performed simultaneous to applying suction either at the tip or near the tip.

In another embodiment the suction is incorporated into the ultrasonic debridement probe to allow for a mechanical disruption and capture of the biofilm. In one embodiment the suction is at the periphery of the ultrasonic debridement probe to allow for maximum capture of the mechanically disrupted biofilm.

In another embodiment, the suction is interspersed throughout the ultrasonic debridement probe so that any area of mechanical disruption has a corresponding area of capture capability.

In another embodiment, a disposable sheath incorporates a suction capability for capturing biofilm during an ultrasonic debridement. In one embodiment the sheath has a multiple position for use during an ultrasonic debridement. The sheath can capture both the debris that is expelled during the debridement and any remaining debris at the surface of the wound bed The sheath can then be disposed of to avoid risk of cross contamination. The sheath may incorporate a sealing strategy to maintain suction pressure while still allowing for multi positioning on the suction tip in relationship to the ultrasonic debridement tip.

Accordingly, a medical therapeutic method pursuant to one aspect of the present invention utilizes an ultrasonic debridement instrument having an operative tip and a suction channel. The method comprises (i) manipulating the instrument to place the operative tip against a patient's tissues at a preselected surgical site, (ii) during contact of the operative tip with the patient's tissues, generating an ultrasonic standing wave in the instrument, thereby fragmenting necrotic tissue and undesired organic material at the surgical site, (iii) during the generating of the ultrasonic standing wave, disposing a suction inlet at a distal end of the suction channel proximate the surgical site and (iv) applying vacuum or negative pressure to the suction channel to remove tissue debris fragmented organic material from the surgical site via the suction inlet, (v) disposing a suction port at a position spaced from the surgical site, and (vi) during and/or after the generating of the ultrasonic standing wave and the fragmenting of tissue and material, sucking ambient air from a region about the surgical site through the suction port at the position.

Preferably, the suction port is provided on the ultrasonic debridement instrument, and the method includes operating an actuator to enable the sucking of air through the suction port.

In one embodiment of the instrument, the actuator may include a sheath or sleeve which is slidably mounted to the instrument for longitudinal motion alternately in opposing directions along the shaft or probe portion thereof. The operating of the actuator then includes shifting the sheath or sleeve in a proximal direction along the instrument. Where the instrument includes a longitudinally shiftable sheath or sleeve, with the suction channel being located between the sheath or sleeve and a shaft or horn of the instrument, the suction inlet and the suction port may both be defined by the distal end of the sheath or sleeve, the position of the sleeve determining whether an intake opening is located at the operative tip of the instrument, and is thus the suction inlet, or is spaced from the operative tip and is therefore the suction port. Accordingly, the method may further comprise shifting the sheath or sleeve in a proximal direction after the applying of a vacuum or negative pressure and prior to the sucking of the ambient air through the suction port, a distal tip of the sheath or sleeve defining the suction inlet in a distal position of the sheath or sleeve, the distal tip defining the suction port in a proximal position of the sheath or sleeve.

In one or more alternative embodiments the suction inlet and the suction port may be different and always mutually spaced from one another. If the instrument includes a slidable sheath or sleeve, the position of that element may determine whether the suction inlet and/or the suction port is active. Thus, the sheath or sleeve may include valves for opening and closing air pathways extending to the suction inlet and the suction port, in dependence on the longitudinal position of the sheath or sleeve. Alternatively, valves may be operated separately via respective electromechanical actuators so that the opening and closing of the suction inlet is controllable independently of the opening and closing of the suction port.

Thus, where the suction port is different from the suction inlet, the suction port being located proximally along the instrument from the suction input, the operating of the actuator may include directing suction under-pressure to the suction port. The actuation may include operating a valve to open a suction pathway to the suction port.

In accordance with another feature of the invention, the method may alternatively or additionally comprise placing an ultrasonic transducer on the patient at least proximate the surgical site after terminating of a debridement process and while the surgical site is free of discernible bacteria. Typically, the transducer is placed immediately after the surgical site has been cleaned of necrotic tissue and other undesirable debris and even prior to the removal of the patient from the operating room. After the placing of the transducer and while the transducer is in effective vibration-transmitting contact with the patient, an electrical energization waveform of an ultrasonic frequency is conducted to the transducer at least intermittently during a period of approximately one day or longer to prevent biofilm formation on the patient at the surgical site and facilitate a healing of the patient's tissue at the surgical site.

The transducer may be affixed to a carrier pad, the placing of the transducer on the patient including attaching the pad to the patient. Alternatively, the transducer may be disposed in a balloon or bladder inflated with a gel or other medium conducive to the effective transmission of ultrasonic pressure waves, the balloon or bladder being attached to the patient over or adjacent the surgical site. Other transducer carriers and methods of attachment to the patient will occur to those skilled in the art.

Accordingly, a medical therapeutic method comprises (a) removing necrotic tissue and undesired organic material from a surgical site on a patient, (b) shortly thereafter, while the surgical site is free of discernible bacteria, placing at least one ultrasonic transducer on the patient at least proximate the surgical site, and (c) after the placing of the transducer and while the transducer is in effective vibration-transmitting contact with the patient, conducting an electrical energization waveform of an ultrasonic frequency to the transducer at least intermittently during a period of approximately one day or longer, the waveform having frequency, amplitude and duration to effectively reduce formation on the patient at the surgical site and thereby facilitate a healing of the patient's tissue at the surgical site. The placing of the transducer preferably includes removably attaching the transducer to the patient atop tissues at the surgical site.

A surgical device comprises an ultrasonic probe having an operative tip, an electromechanical transducer operatively connected to the probe for generating an ultrasonic standing wave in the probe, and at least one sheath or sleeve disposed about the probe and defining at least a first suction port at a distal end of the probe, proximate the operative tip, and a second suction port spaced from the distal end of the probe.

The one or more sheaths or sleeves may take the form of exactly one sheath or sleeve slidably attached to the probe to shift between a distal position and a proximal position, wherein a distal end of the sheath or sleeve is alternately locatable (i) proximate the operative tip to define the first suction port and (ii) at a predetermined distance from the operative tip to define the second suction port.

Alternatively, the first suction port and the second suction port are different openings in the at least one sheath or sleeve. Their operational status may be separately controlled via respective valves. Moreover, the suction ports may be connectable to vacuum sources of different strengths. The magnitude of the vacuum or negative pressure applied to the proximal port is typically greater than the magnitude of the vacuum or negative pressure applied to the distal port.

The sheath or sleeve may define a first suction channel extending to the first suction port and a separate second suction channel extending to the second suction port, the first suction channel and the second suction channel being subjectable to different negative pressures.

Described herein is a method for bacterial containment during application of therapeutic ultrasound application. In a preferred embodiment, a suction device is incorporated adjacent to the therapeutic ultrasound applicator to create a path of removal for any bacteria that is being displaced during the treatment. The suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. The suction device can also be used to contain irrigation spray that results from the application of therapeutic ultrasonic energy.

In another embodiment the suction device is integrated into the treatment probe so that is has ports of capture that are strategically placed to remove bacteria that is displaced during tissue removal during debridement. The suction device is incorporated in such a way as to orient the orifice of the suction to favorably capture any projected, predicted or anticipated paths of spray the would result from the applicator tip interacting with the targeted treatment site. The suction device can also be used to contain irrigation spray that results from the application of therapeutic ultrasonic energy.

In another embodiment the suction device is separate from the treatment probe but is used in coordination to capture any bacteria that is displaced by the tissue removal during debridement. The suction device can be strategically placed adjacent to the treatment area in such a manner that the opening of the suction device creates a preferential path for the capture of displaced bacteria. The suction device can be a ring that defines a specific treatment area around the ultrasound applicator. The ring device has capture ports that are oriented inward towards the potential treatment areas so that in any direction capture of bacteria that is displaced from the treatment site. The suction device is incorporated in such a way as to orient the orifice of the suction to favorably capture any projected, predicted or anticipated paths of spray the would result from the applicator tip interacting with the targeted treatment site. The suction device can also be used to contain irrigation spray that results from the application of therapeutic ultrasonic energy. The suction device can be secured to the patient temporarily so that it creates a barrier for the bacteria or irrigation spray to be able to get beyond. The temporary attachment can be a strap, a skin friendly adhesive pad, or another easy to place easy to remove approach.

In another embodiment, a suction device is incorporated adjacent to the therapeutic ultrasound applicator to create a path of removal for any bacteria that is being displaced during the treatment. The suction device has two or more position of use. In the first position the suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. In the second position the suction device is incorporated in such an way to come into direct contact with the targeted treatment surface to allow for direct removal of any residual bacteria. The suction device can also be used to contain irrigation spray that results from the application of therapeutic ultrasonic energy.

In another embodiment suction device is incorporated into a therapeutic ultrasound applicator that delivers an irrigation stream to the applicator tip. The suction device is a disposable sheath incorporated adjacent to the therapeutic ultrasound applicator to create a path of removal for any bacteria or irrigation spray that is being displaced during the treatment. The suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. The suction device can also be used to contain irrigation spray that results from the application of therapeutic ultrasonic energy.

In another embodiment suction device is incorporated into a therapeutic ultrasound applicator that delivers an irrigation stream to the applicator tip. The suction device is a disposable sheath that is molded onto the single use ultrasound treatment probe to create a path of removal for any bacteria or irrigation spray that is being displaced during the treatment. The suction device is incorporated in such a way as to orient the orifice of the suction to favorably capture any projected, predicted or anticipated paths of spray the would result from the applicator tip interacting with the targeted treatment site. In this the suction device is optimized for the preferential capture of any bacteria that is displaced by the tissue removal during debridement. The suction device can also be used to contain irrigation spray that results from the application of therapeutic ultrasonic energy.

BRIEF DESCRIPTION OF THE DRAWINGS

FIG. 11 is an exploded right side, top and front perspective view of a probe and sheath included in the device of FIGS. 9 and 10.

FIG. 12 is an exploded left side, top, and rear perspective view of the probe and sheath of FIGS. 9-11.

FIG. 13 is a rear elevational view of the probe and sheath of FIGS. 9-12.

FIG. 19 is a schematic perspective view of a suction device in accordance with the present invention, in place around a surgical site.

DETAILED DESCRIPTION

Figure 1:
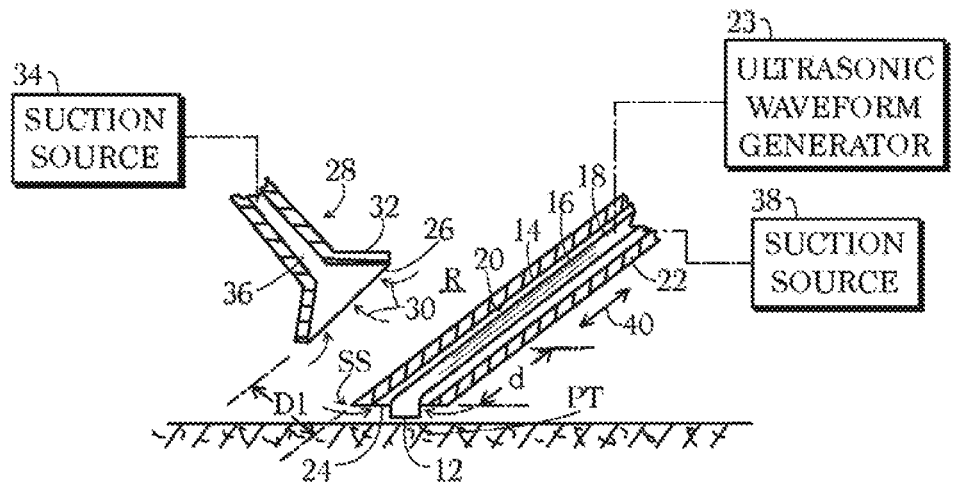
FIG. 1 is partially a schematic cross-sectional view and partially a block diagram of a system for removing biofilm from a wound site and reducing the likelihood of biofilm reformation thereafter.

The present disclosure contemplates a two phase method for reducing the formation of biofilm. The first phase is performed where a wound site is being treated for removal of necrotic tissue, eschar or biofilm and includes an evacuation of ambient air from a region about the surgical or treatment site, to extract airborne or aerosolized bacteria ejected from the site by the treatment. The extracted bacteria are prevented from settling back onto the cleansed tissue surface, thus at least reducing colonial bacteriological growth and concomitantly exuded biofilm material. The second phase or approach for reducing biofilm involves the attachment of one or more ultrasonic transducers to the patient over or near a surgical treatment site after the surgery is terminated. Each applied ultrasonic transducer is used to vibrate the patient's tissues at the treatment site to disrupt biofilm formation. The two phases of treatment may be used separately depending on the application. Thus, ultrasonic biofilm disruption may be used at wound sites which have not been subjected to formal processes for removal of necrotic tissue, eschar or biofilm.

Accordingly, a medical therapeutic method may utilize an ultrasonic debridement instrument 10 (FIG. 1) having an operative tip or surface 12 and a suction channel 14 defined between an outer surface 16 of an ultrasonic horn 18 and an inner surface 20 of a cannula or sheath 22. The method comprises manipulating the instrument 10 to place the operative tip or surface 12 against a patient's tissues PT at a preselected surgical site SS. During contact of the operative tip 12 with the patient's tissues PT, one operates a waveform generator 23 to generate an ultrasonic standing wave in the instrument 10 and particularly in probe or horn 18, to thereby fragment necrotic tissue and undesired organic material at the surgical site SS. During the generating of the ultrasonic standing wave, a suction inlet 24 at a distal end of the suction channel 14 is disposed proximate the surgical site SS and a vacuum or negative pressure is applied to the suction channel 14 to suck tissue debris and fragmented organic material from the surgical site SS via the suction inlet 24. A suction port 26 of another instrument 28 is disposed at a position spaced at a distance D1 from the surgical site SS. During and/or after the generating of the ultrasonic standing wave and the fragmenting of tissue and material by instrument 10, instrument 28 is operated to suck ambient air, as indicated by arrows 30, from a region R about the surgical site SS through suction port 26. While suction inlet 24 is typically located between 1 and 5 mm from the surgical site SS and the tissue surface at the surgical site, suction port 26 is typically located 2-6 cm from the tissue surface at the surgical site SS.

As depicted in FIG. 1, instrument 28 may be formed at a distal end with an enlarged or expanded extension 32, such as a cone, to funnel air 30 into the instrument. A suction source or vacuum generator 34 communicating with a lumen 36 of instrument 28 may exert a greater suction force than that of a suction source or vacuum generator 38 communicating with suction channel 14.

In an alternative approach, instrument 28 is omitted. Instead, cannula or sheath 22 is shiftably mounted to probe or horn 18 for longitudinal motion alternately in opposing directions along the shaft or probe portion thereof, thereby enabling the user to position the suction port, defined in part by the distal edge of the sheath, in two or more alternative locations, a most distal location adjacent the operative tip 18 of the probe or horn 12 and a more proximal location. As indicated by a double headed arrow 40, cannula or sheath 22 is pulled in a proximal direction after an operation removing tissue or other organic matter from surgical site SS so that suction port 26 is located at a distance d from the operative tip or surface 12 of instrument 10. An actuator such as suction source 38, or a switch component thereof, is operated to enable the sucking of air through suction port 26 at the retracted position of cannula or sheath 22. In a simple configuration, suction source 38 may have twp operating states, on and off, the position of sheath 22 determining whether suction is applied at the surgical site SS or at a distance therefrom. In a slightly more complicated configuration, suction source 38 may be provided with three operating states, namely, off, high suction and low suction. The degree of suction may be selectable by the operator or may be automatically controlled in accordance with the longitudinal or axial position of sheath 22 along probe or horn 12. For instance, sheath or sleeve 22 may be provided with valves (not shown) for opening and closing air pathways in dependence on the longitudinal position.

Figure 2:
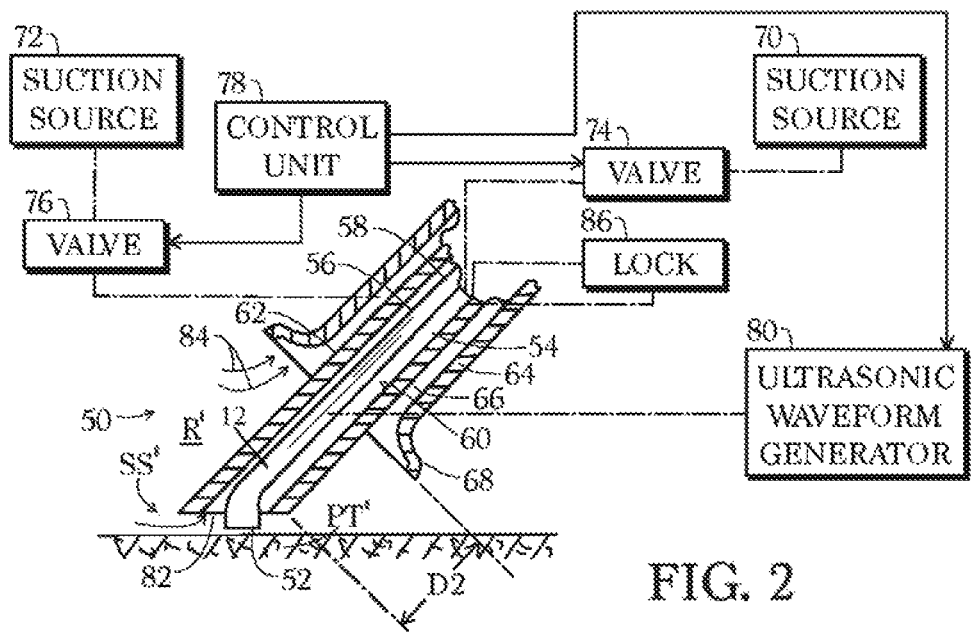
FIG. 2 is partially a schematic cross-sectional view and partially a block diagram of another apparatus for removing biofilm from a wound site and reducing the likelihood of biofilm reformation thereafter.

An alternative instrument assembly 50 depicted in FIG. 2 has an operative tip or surface 52 and a suction channel 54 located between an outer surface 56 of an ultrasonic horn 58 and an inner surface 60 of a first or inner sheath 62. A second, outer, sheath 64 surrounds the first sheath 62 and defines therewith a second suction channel 66 for the evacuation of ambient air from a sizable region R' about the surgical site, exemplarily through a conical port element 68 at the distal end of the outer sheath 64. The two suction channels 54 and 66 may be connected to respective suction sources or vacuum generators 70 and 72 via respective valves 74 and 76 both actuatable by the operator via a control unit 78. Control unit 78 is tied to a control input (not separately designated) of an ultrasonic waveform generator 80 that is operatively connected to probe or horn 12 via an electromechanical transducer (not shown) such as a stack of piezoelectric crystals. Control unit 78 may be programmed to open valve 76 within a selectable time interval after the opening of valve 74 and the activation of waveform generator 80.

In a surgical procedure, instrument assembly 50 is manipulated to place the operative tip or surface 52 against patient's tissues PT' at a preselected surgical site SS'. During contact of the operative tip 52 with the patient's tissues PT', control unit 78 is operated to activate waveform generator 80, which generates an ultrasonic standing wave in probe or horn 58, to thereby fragment necrotic tissue and undesired organic material at the surgical site SS'. During the generating of the ultrasonic standing wave, a suction inlet 82 at a distal end of inner suction channel 54 is disposed proximate the surgical site SS' and a vacuum or negative pressure is applied by suction source 70 to the suction channel 54 via valve 74 to suck tissue debris and fragmented organic material from the surgical site SS' through the suction inlet 82. Conical port element 68 is disposed at a distance D2 from the surgical site SS'. During and/or after the generating of the ultrasonic standing wave and the fragmenting of tissue and material by instrument 50, vacuum generator 72 and valve 76 are actuated by control unit 78 to suck ambient air, as indicated by arrows 84, from region R' through suction port or cone 68. Suction inlet 82 is typically located a minimal distance, exemplarily between about 1 and about 5 mm, from tissues at the surgical site SS' while suction port 68 distance D2 is typically 2-6 cm from the surgical site SS'.

Outer sheath 64 may be temporarily fixed to inner sheath 62 via a quick-release lock 86 such as a set screw. Thus, the relative axial positions of sheaths 62 and 64 may be adjusted to change distance D2. Control unit 78 may be connected to suction sources or vacuum generators 70 and 72 for varying the power usage thereof and average magnitudes of the negative pressures generated thereby.

Figure 3:
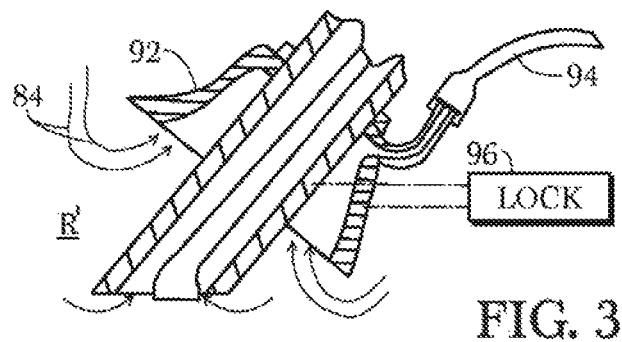
FIG. 3 is partially a schematic cross-sectional view and partially a block diagram of yet a further apparatus for removing biofilm from a wound site and reducing the likelihood of biofilm reformation thereafter.

FIG. 3 illustrates a modification of the instrument assembly 50 of FIG. 2. Instead of outer sheath 64, a suction nozzle 92 is attached to sheath 62. Nozzle 92 is connected to suction source or vacuum generator 72 via a reinforced hose 94. Nozzle 92 is removably secured to sheath 62 via a locking element 96 such as a ring clamp or a set screw. The operation of modified instrument 90 is as discussed above.

The present method alternatively or additionally comprises placing an ultrasonic transducer 102 (see, e.g., FIGS. 4 and 5) in effective contact with a patient TP at least proximate a surgical site SI after terminating of a debridement or other tissue cleaning procedure and while the surgical site SI is free of discernible bacteria. Typically, transducer 102 is placed immediately after the surgical site SI has been cleaned of necrotic tissue and other undesirable debris and even prior to the removal of the patient TP from the operating room. After the placing of transducer 102 and while the transducer is in effective vibration-transmitting contact with the patient TP, an electrical energization waveform of an ultrasonic frequency is conducted from a waveform generator 104 to transducer 102 at least intermittently during a period of approximately one day or longer to reduce, if not prevent, biofilm formation on the patient at the surgical site SI and thereby facilitate a healing of the patient's tissue at the surgical site.

Figure 4:
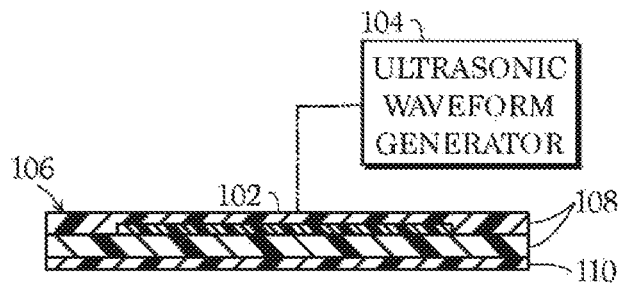
FIG. 4 is partially a schematic cross-sectional view and partially a block diagram of a device for attachment to a patient at a wound site, to reduce the likelihood of biofilm formation on the wound site.
Figure 5:
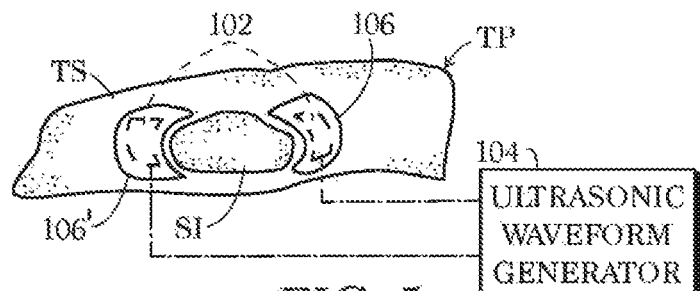
FIG. 5 is a schematic top plan view and partially a block diagram of the device of FIG. 4, in position and attached to a patient at a wound site on the patient.
Figure 6:
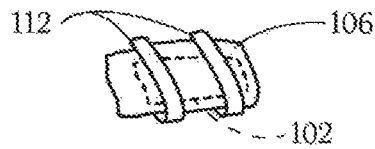
FIG. 6 is a schematic perspective view of another device for attachment to a patient at a wound site, to reduce the likelihood of biofilm formation.

As depicted in FIG. 4, transducer 102 may be affixed to a carrier pad 106, exemplarily sandwiched between layers 108 of a biocompatible and ultrasound transmitting material. The placing of transducer 102 on the patient TP preferably includes attaching pad 106 to the patient, for example, via an adhesive layer 110. As depicted in FIG. 5, pad 106 is disposed alone or together with one or more other carrier pads 106', on a tissue surface TS proximate surgical site SI. Alternatively, pad 106 may be placed directly over the surgical site SI shortly, if not immediately, after tissue removal is complete. In that case adhesive layer 110 may be omitted in favor of a layer of gel. The gel may be oxygenated and contain antibiotics. As depicted in FIG. 6, straps or bands 112 may be provided for securing the pad 106 to the patient TP.

Figure 7:
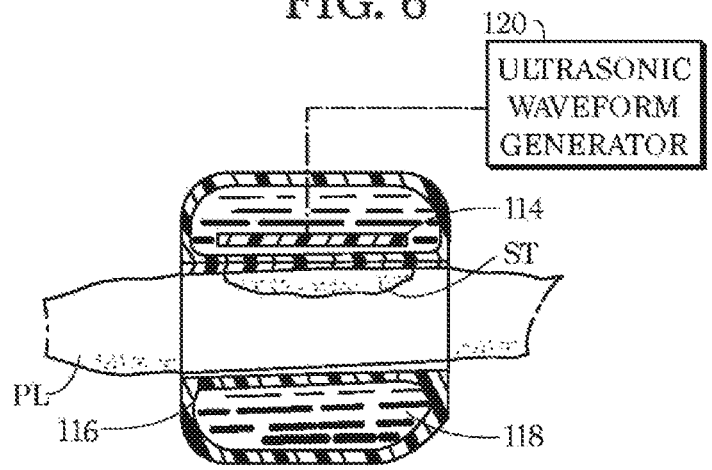
FIG. 7 is partially a schematic cross-sectional view and partially a block diagram of a device for attachment to a patient at a wound site, to reduce the likelihood of biofilm formation on the wound site, showing attachment of the device to a patient's limb.

Alternatively, as depicted in FIG. 7, an electromechanical, specifically, a piezoelectric, transducer 114 may be disposed inside a balloon or bladder 116 inflated with a gel or other medium 118 conducive to the effective transmission of ultrasonic pressure waves, the balloon or bladder being attached to a patient TP' over or adjacent a surgical site SI'. Balloon or bladder 116 is affixed to a patient, e.g., around an arm or leg PL, over or near a surgical site ST and an ultrasonic waveform generator 120 is activated to generate ultrasonic vibrations conducted into the patient's tissue to disrupt biofilm formation. Other transducer carriers and methods of attachment to the patient will occur to those skilled in the art.

A medical therapeutic method utilizing one or more of the transducer devices shown in FIGS. 4-7, first comprises cleaning surgical site SI or ST of necrotic tissue and undesired organic material, for instance via ultrasonic debridement and suction as discussed above with reference to FIGS. 1-3. Shortly thereafter, while the surgical site SI or ST is free of discernible bacteria, one places at least one ultrasonic transducer 102, 114 on the patient TP, TP' proximate or on the surgical site SI, ST, and thereafter, while the transducer is in effective vibration-transmitting contact with the patient TP, TP', conducting an electrical energization waveform of an ultrasonic frequency to the transducer 102, 114 at least intermittently during a period of approximately one day or longer. The waveform has frequency, amplitude and duration parameters selected to effectively reduce biofilm formation on the patient TP, TP' at the surgical site SI, ST and thereby facilitate a healing of the patient's tissue at the surgical site. The ultrasound generates a surface acoustic wave, exemplarily at 20 kHz, illustratively with an acoustic power output of 0.2-0.4 w/cm$^2$. The treatment period is long enough to enable healthy tissue formation. The placing of the transducer 102, 114 preferably includes removably attaching the transducer to the patient atop tissues at the surgical site SI, ST.

Figure 8:
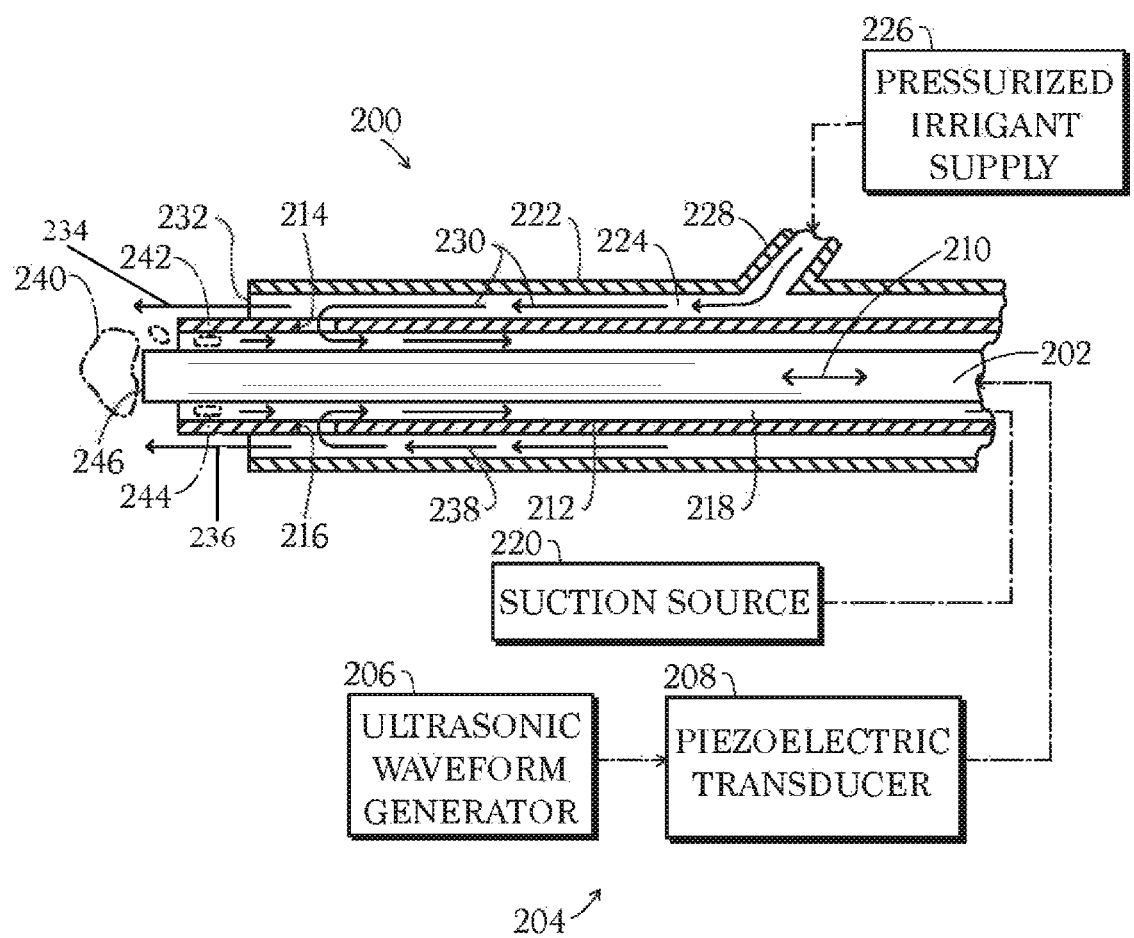
FIG. 8 is a schematic longitudinal cross-sectional view of a distal end portion of an ultrasonic instrument assembly in accordance with the resent invention.

As depicted in FIG. 8, an ultrasonic surgical device 200 comprises an ultrasonic probe 202 that is operatively connected to a source 204 of ultrasonic vibratory energy including an ultrasonic signal generator 206 and a stack of piezoelectric crystals 208 for vibrating at an ultrasonic frequency as symbolized by a double-headed arrow 210. Probe 202 extends longitudinally through an inner sheath 212 that is provided at a distal end region with one or more apertures 214, 216. Probe 202 and sheath 212 define an annular inner channel 218 that is connected at a proximal end of the instrument to a suction or vacuum source 220. An outer sheath 222 surrounds the inner sheath 212 and defines therewith an annular outer channel 224.

During use of the surgical device or assembly 200 of FIG. 8, irrigant flows from a supply 226 through an inlet port 228 and into outer channel 224, as indicated by arrows 230. The irrigant exits the outer channel 224 along two paths, firstly through a distal end opening 232, per arrows 234, 236, and secondly through apertures 214, 216 into inner channel 218 where the liquid or irrigant is drawn in a proximal action, as indicated by arrows 238, toward suction source 220.

At a surgical site 240, tissue fragments 242 and 244 are separated by ultrasonic vibration of a distal end surface 246 of probe 202 placed into contact with the surgical site. A vacuum underpressure at the distal end (not designated) of inner channel 218 draws tissue fragments 242, 244 into the inner channel, together with irrigant present at the surgical site 240 owing to outflow from outer channel 224 via distal end opening 232. Further irrigant entering inner channel 218 via apertures 214, 216 facilitates emulsion flow.

Device or assembly 200 is different from surgical aspirators where disrupted tissue is being aspirated through the center of a mostly cylindrical cannulated probe or small cross-section. In device 200 of FIG. 8, the dual irrigant capture scheme facilities the delivery of sufficient liquid to ensure the occurrence of cavitation as well as to maintain safe temperature levels of both the probe 202 and the tissue at the surgical site 240. By capturing liquid via apertures 214, 216, before the irrigant can reach the surgical site 240, the device 200 reduces the volume of liquid that could be atomized by the probe 202.

The reduction of atomized irrigant is even more desirable in wound debridement procedures. This is due to the much larger size of the probe tip area normally used for large scale debridement, which is up to 80 times that of surgical aspirator probes, and also due to the larger volumes of irrigant required to maintain safe temperature levels in the tissue and probe.

Figure 9:
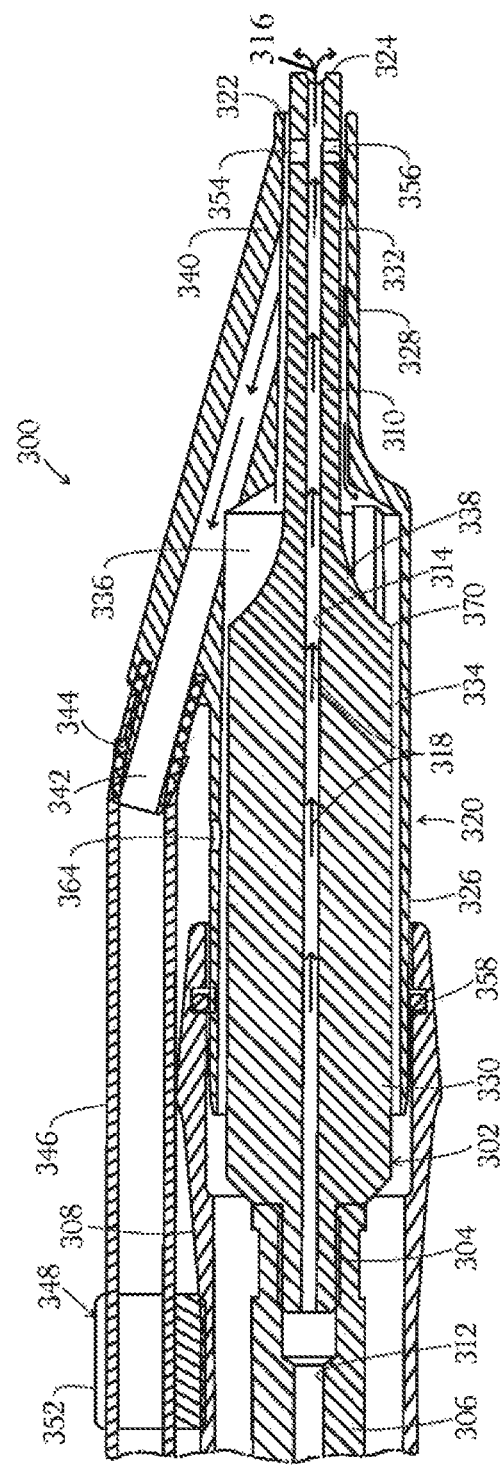
FIG. 9 is a partial longitudinal cross-sectional view of a device for debriding or removing biofilm from a wound site in accordance with the present invention.
Figure 10:
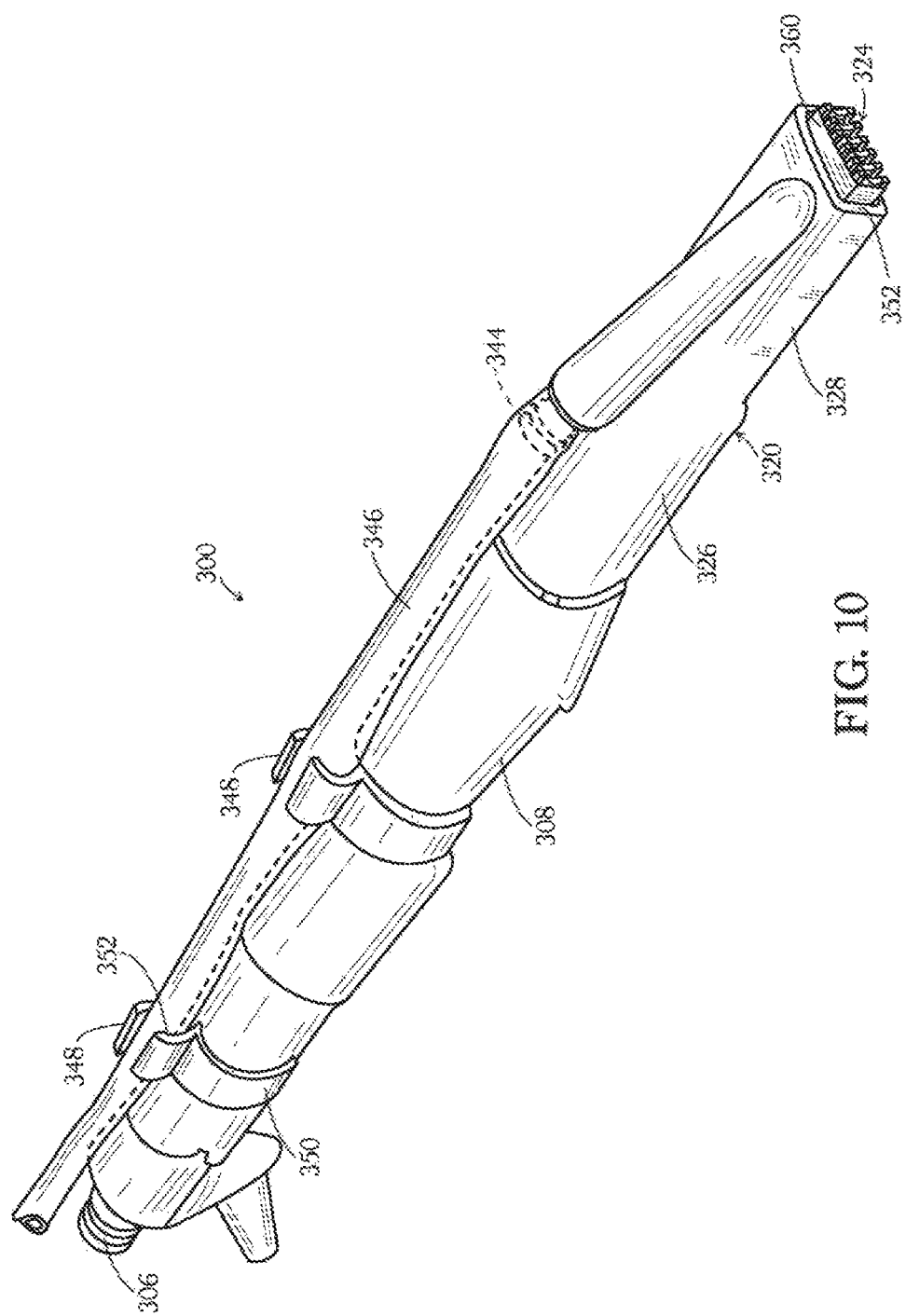
FIG. 10 is a schematic right side, top and front perspective view of the device of FIG. 9.
Figure 14:
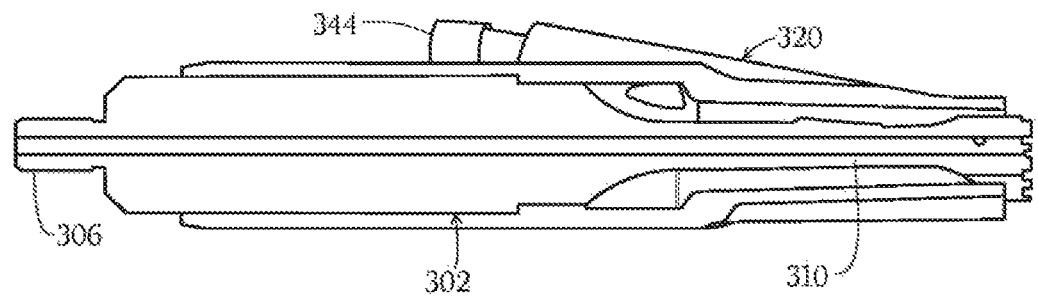
FIG. 14 is a partial cross-sectional view, similar to FIG. 9, taken along line XIV-XIV in FIG. 13.
Figure 15:
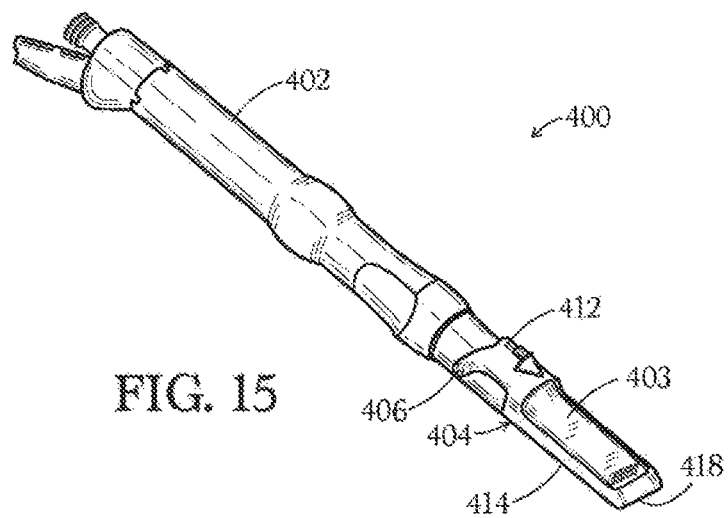
FIG. 15 is a right side, top and front perspective view of another device for debriding or removing biofilm from a wound site in accordance with the present invention.
Figure 16:
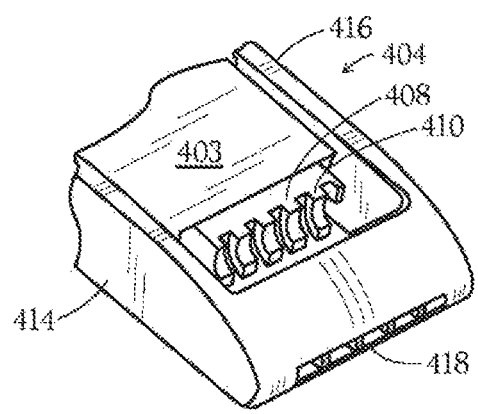
FIG. 16 is a partial right side, top and front perspective view, on an enlarged scale, of a distal tip portion of the device of FIG. 15.
Figure 17:
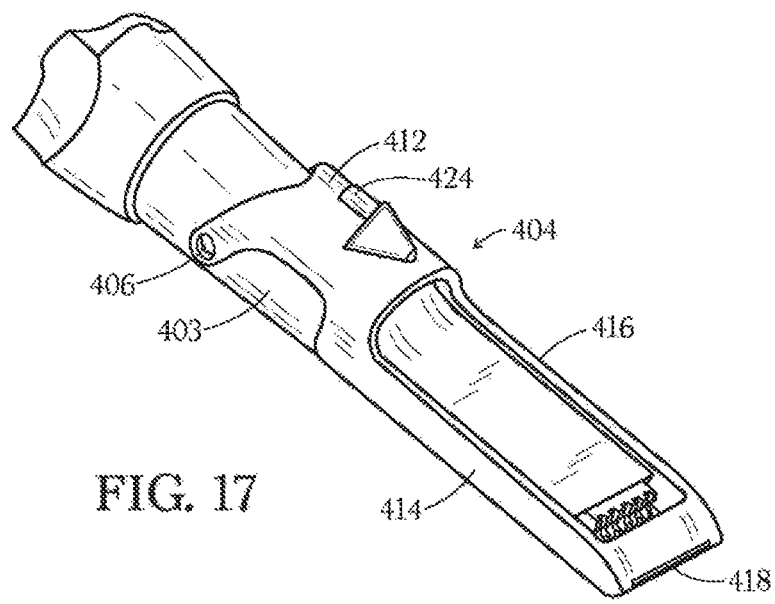
FIG. 17 is a partial right side, top and front perspective view, on an enlarged but intermediate scale, of a distal end portion of the device of FIGS. 15 and 16.

As depicted in FIGS. 9 and 10, a surgical device 300 for debriding or removing biofilm from a wound site comprises an ultrasonic probe 302 which is attached at a proximal end via threaded connector 304 to a driver 306 is operatively connected to a generator of vibratory energy, typically a piezoelectric transducer array (not shown). Both the driver 306 and the piezoelectric transducer are located in a handpiece which has a cover or housing (not shown) connected to a casing 308. Probe 302 tapers down on a distal side to a distal end section 310. It is to be noted that the terms "horn" and "probe" are used synonymously.

Driver 306 and probe 302 are formed with mutually aligned axial channels or bores 312 and 314 that define a lumen (not separately designated) for the delivery of irrigant to a distal end aperture 316 in probe horn section 310, as indicated by flow arrows 318.

Surgical device 300 further includes a rigid sheath 320 that is shiftably mounted to casing 308 to vary a position of a distal tip 322 of the sheath relative to a distal tip or end face 324 of probe 302. Sheath 320 includes a cylindrical rear section 326 and a rectangularly prismatic forward section 328, which correspond geometrically to cross-sections of horn 310 and a proximal portion 330 of probe, 302, respectively.

Together with an outer surface (not designated) of probe horn 310, forward sheath section 328 defines a forward or distal channel or conduit 332, which is rectangular in cross-section. Together with an outer surface (not designated) of proximal probe portion 330, rear sheath section 326 defines a rearward or proximal channel or conduit 334, which is circular in cross-section. At a distal end, rearward channel 334 expands to an enlarged space 336 owing to the tapering of the probe at 338.

Sheath 320 is provided with an arm 340 that is connected at a forward or distal end to forward section 326 and is angled outwardly at a proximal side. Sheath arm 340 includes a main aspiration channel 342 that communicates at a distal end with forward channel 332. At a more proximal location, aspiration channel 342 of arm 340 communicates with rearward channel 334 and more particularly with enlarged space 336. At a proximal end, arm 340 is provided with an undercut connector port 344 which receives a resilient aspiration tube 346 in a friction fit. Aspiration tube 346 is fastened to casing 308 via a pair of clips 348 each formed with a pair of slotted annular rings 350 and 352 for receiving casing 308 and aspiration tube 346, respectively.

At a forward or distal end, probe horn 310 is formed with one or more apertures or cross-bores 354 and 356 that communicate on an inner side with channel or lumen 314 and on an outer side with forward channel 332. At a rear end, rear section 326 of sheath 320 is inserted between proximal probe portion 330 and a distal end of casing 308. An O-ring seal 358 is provided between casing 308 and an outer surface of sheath rear section 326.

A distal end of horn section 310 is formed into a probe head 360 that is extended in a traverse dimension, orthogonally to a longitudinal axis of the probe 302. Head 360 may particularly take a form disclosed in U.S. patent application Ser. No. 14/172,566, Publication No. 2015/0216549, the disclosure of which is incorporated by reference herein. In particular, head 360 includes a plurality of teeth 362 arranged in two mutually parallel rows along opposing edges or sides of the distal end face 324 of the probe head.

As indicated above, sheath 320 is slidable or longitudinally shiftable relative to probe 302 so as to be continuously adjustable as to axial or longitudinal position relative to probe head 360 anywhere from a fully extended position, where the distal tip 322 of sheath 320 is essentially coplanar with the distal end face 324 of probe head 360, to a retracted position where at least the teeth 362 of probe head 360 are fully exposed. O-ring 358 enables the adjustable positioning of sheath 320.

Apertures or cross-bores 354 and 356 serves as bypass holes, regardless of the relative longitudinal positioning of sheath 320 and probe 302. A vacuum under-pressure applied to the internal spaces of sheath 320, i.e., aspiration channel 342, forward channel 332, and rearward channel 334, by a suction source (not shown) enables the capturing and removal of most of the irrigant that is delivered through central channel 314 (flow arrows 318). Accumulation of irrigant within sheath 320, especially when the device is used in a predominantly vertical orientation, is prevented by the provision of two suction pathways, namely, between aspiration channel 342 and each of the forward channel 332 and rearward channel 334. Irrigant not captured via a distal pathway is captured in a proximal pathway.

Where tissue fragments are small enough to be aspirated through the gap between the probe 302 and the sheath 320, clogging is prevented by designing the aspiration pathway of channel 324 to gradually increase in cross-sectional area from the probe-sheath gap at the distal end of the instrument all the way to the aspiration line. A vent port 364 may be provided in the rear sheath section 326 to reduce the magnitude of vacuum-generated pull force acting on the tissue which is driven towards and into the probe-sheath gap during debridement.

Matching or cooperating features 366 and 368 are respectively disposed on the outer side of the probe 302 and the inside of rear sheath section 326, in close proximity to a nodal plane or the probe, to facilitate probe-sheath alignment. This minimizes the chances of a probe-sheath contact at the points of maximum vibratory motion (antinodes), particularly at end face 324 of probe head 360. Due to their placement at a location of minimal vibratory displacement, e.g., the junction 370 between cylindrical probe portion 330 and tapering probe section 338, the alignment features 366 and 368 allow for the probe-sheath contact necessary for preventing or minimizing the unwanted interaction in the area of maximum vibratory displacement.

As depicted in FIGS. 15-18, another ultrasonic surgical device 400 for debriding or removing biofilm from a wound site comprises a handpiece 402 provided at a distal end with a sheath 403 and a suction or evacuation attachment 404 swingably attached to the sheath at pivot pins 406 (only one shown). An ultrasonic probe is disposed inside handpiece 402 and sheath 403 and terminates and a distal end in a head 408 formed with crenulations or teeth 410.

Figure 18:
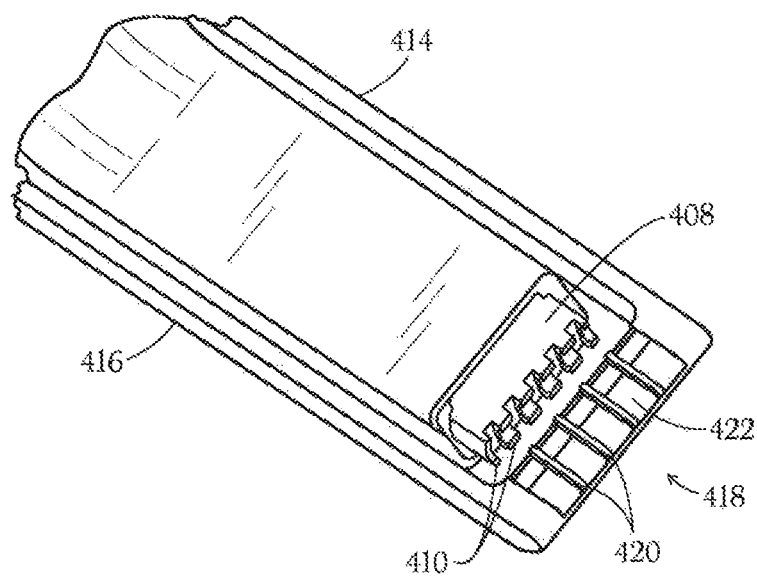
FIG. 18 is a left side, bottom, and front perspective view, on an enlarged scale, of the device of FIGS. 15-17.

Suction attachment 404 includes a body portion 412 at a proximal end and a pair of hollow arms 414, 416 extending in a distal direction from the body portion. Arms 414 and 416 are joined to one another at their distal end by a cross-piece 418 serving as a suction head. As shown in FIG. 18, suction head 418 is formed on a lower side with a plurality of longitudinally extending runners or ribs 420 and a recess 422, which is bridged by the runners or ribs and which communicated with aspiration channels (not shown) in the hollow arms 414, 416. Body portion 412 is provided with a port connector 424 to which an aspiration tube (like tube 346) is attached. Liquid irrigant is guided to an outlet port (not shown) in probe head 408 via a channel (not shown) in the probe. The irrigant, together with tissue fragments and other surgically generated debris, is drawn from the surgical site via suction attachment 404. More particularly, during a debridement operation, suction head 418 is placed in essential contact with the tissue at the surgical site. Irrigant and tissue debris are collected via recess 422 and guided through arms 414 and 416 and out through port connector 424.

The pivotable mounting of suction attachment 404 enables suction head 418 and particularly recess 422 to remain juxtaposed to a tissue surface even as the rest of the instrument particularly handpiece 402, sheath 403 and the probe are tilted to assume different angles relative to a normal to the tissue surface.

FIG. 19 shows a suction device 500 in the form of a ring that is placed on a tissue surface 502 for purposes of removing airborne particles generated by use of an ultrasonic instrument 504 on tissue at a surgical site 506. Ring 500 is provided along an inner cylindrical surface with a plurality of spaced suction ports 508. Ports 508 may be tiltably mounted to the ring 500, e.g., via universal joints that have joint balls 509 that are perforated. Ring 500 is at least partially hollow so that suction ports 508 may communicate via a hose 510 with a suction source (not shown). Ring 500 may be attached to a patient, e.g., to a limb 512, via one or more of various coupling devices, such as a strap 514 with buckles or hook-and-loop fabric fasteners, or an adhesive layer 516.

Although the invention has been described in terms of particular embodiments and applications, one of ordinary skill in the art, in light of this teaching, can generate additional embodiments and modifications without departing from the spirit of or exceeding the scope of the claimed invention. Moreover, the phase shift might be varying, for instance, where the vibration modes are of different frequencies. Accordingly, it is to be understood that the drawings and descriptions herein are proffered by way of example to facilitate comprehension of the invention and should not be construed to limit the scope thereof.

What is claimed is:

1. A medical therapeutic method comprising:
   providing an ultrasonic debridement instrument having an operative tip;
   manipulating said instrument to place said operative tip in effective proximity to a patient's tissues at a preselected surgical site;
   after placing of said operative tip in effective proximity to the patient's tissues, generating an ultrasonic standing wave in said instrument, to thereby fragment necrotic tissue and other undesired organic material at said surgical site;
   placing at least one ultrasonic transducer on the patient at least proximate the surgical site after terminating of a debridement process and while the surgical site is free of discernible bacteria; and
   after the placing of said transducer and while said transducer is in effective vibration-transmitting contact with the patient, conducting an electrical energization waveform of an ultrasonic frequency to said transducer at least intermittently during a period of approximately one day or longer to at least reduce biofilm formation on the patient at the surgical site and facilitate a healing of the patient's tissue at the surgical site.

2. The method defined in claim 1 wherein said transducer is affixed to a carrier pad, the placing of said transducer on the patient including attaching said pad to the patient.

3. The method defined in claim 1, further comprising utilizing said instrument at a lower energy setting to pre-condition the tissues at the surgical site for disrupting adherence or starting the formation of biofilm.

4. A medical therapeutic method comprising:
ultrasonically removing necrotic tissue and other undesired organic material from a surgical site on a patient;
after the removal of all discernible necrotic tissue and other undesirable organic material from the surgical site and while the surgical site is free of discernible bacteria, placing at least one ultrasonic transducer on the patient spaced from the surgical site; and
after the placing of said transducer and while said transducer is in effective vibration-transmitting contact with the patient, conducting an electrical energization waveform of an ultrasonic frequency to said transducer at least intermittently during a period of approximately one day or longer, said waveform having frequency, amplitude and duration to effectively reduce biofilm formation on the patient at the surgical site and thereby facilitate a healing of the patient's tissue at the surgical site.

5. The method defined in claim 4 wherein the placing of said transducer includes removably attaching said transducer to the patient.

6. The method defined in claim 5 wherein the placing of said transducer includes removably attaching said transducer atop tissues spaced from the surgical site.

7. The method defined in claim 5 wherein said transducer is affixed to a carrier pad, the placing of said transducer on the patient including attaching said pad to the patient.

8. The method defined in claim 4 wherein the removing of necrotic tissues includes operating an ultrasonic debrider instrument at a first energy setting, further comprising utilizing said instrument at a lower second energy setting to pre-condition the tissues at the surgical site for disrupting adherence or starting the formation of biofilm.

\* \* \* \* \*